United States Patent
Anton et al.

(10) Patent No.: US 8,803,113 B2
(45) Date of Patent: Aug. 12, 2014

(54) SCRAPER FOR AN APPLICATOR TO BE USED IN ELECTRON RADIATION THERAPY AND APPLICATOR

(75) Inventors: Gisela Anton, Erlangen (DE); Björn Kreisler, Erlangen (DE); Torsten Müller, Regensburg (DE); Ina Ritter, Erlangen (DE); Gabriele Suft, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 145 days.

(21) Appl. No.: 13/415,699

(22) Filed: Mar. 8, 2012

(65) Prior Publication Data

US 2012/0292538 A1 Nov. 22, 2012

(30) Foreign Application Priority Data

Mar. 11, 2011 (DE) .......................... 10 2011 005 450

(51) Int. Cl.
*G21F 3/00* (2006.01)
*G21K 1/02* (2006.01)
*A61N 5/10* (2006.01)

(52) U.S. Cl.
CPC ................ *A61N 5/1077* (2013.01); *G21K 1/02* (2013.01); *A61N 2005/1089* (2013.01); *A61N 2005/1095* (2013.01)
USPC ................... 250/515.1; 250/505.1; 250/492.3

(58) Field of Classification Search
CPC .................................. G21F 3/00; H01J 33/00
USPC ........................................................ 250/515.1
See application file for complete search history.

(56) References Cited

U.S. PATENT DOCUMENTS 6,674,087 B2 * 1/2004 Cadwalader et al. ...... 250/515.1

OTHER PUBLICATIONS

Battum, et al, "Scattered radiation from applicators in clinical electron beams", Phys. Med. Biol. 48 (2003) pp. 2493-2507.*
L.J. van Battum, et al., "Scattered radiation from applicators in clinical electron beams," Phys. Med. Biol. 48, pp. 2493-2507, 2003.
"Radiation Dosimetry: Electron Beams with Energies Between 1 and 50 MeV," ICRU Report 35, Issued Sep. 15, 1984, Second Reprinting May 30, 1992, pp. 43-47, 1984.

* cited by examiner

*Primary Examiner* — Phillip A Johnston
(74) *Attorney, Agent, or Firm* — Lempia Summerfield Katz LLC

(57) ABSTRACT

A scraper for an applicator to be used in electron radiation therapy includes a three layer arrangement. A first layer of the three layer arrangement faces an incident direction of electrons and consists of a first material of a first atomic number. The first atomic number is smaller than a second atomic number of a second material of a second layer of the three layer arrangement. The second atomic number is smaller than a third atomic number of a third material of a third layer of the three layer arrangement. The third layer faces away from the incident direction of the electrons.

12 Claims, 1 Drawing Sheet

SCRAPER FOR AN APPLICATOR TO BE USED IN ELECTRON RADIATION THERAPY AND APPLICATOR

This application claims the benefit of DE 10 2011 005 450.2, filed on Mar. 11, 2011.

BACKGROUND

The present embodiments relate to a scraper for an applicator to be used in electron radiation therapy.

Radiation with electrons is used in medicine for treatment (e.g., for the treatment of tumors). Electrons are accelerated in linear accelerators. The beam is extended and flattened (e.g., by scatter films). In order to shape the electron beam, collimator units and/or scrapers that laterally delimit the beam are provided in this area.

Electrons, for example, are significantly scattered by air and other materials so that a directional distribution and a spatial distribution of the electrons in the beam is "obliterated." Consequently, the electron beam is recollimated adjacent to a surface to be irradiated (e.g., the skin of a patient). With electron radiation in the medical field, electron applicators that delimit the dimensions of the electron beam adjacent to the patient in order to reduce the divergence of the beam and, for example, to protect the healthy tissue, are provided.

Electron applicators are known in various designs, common to all of which being that the electron applicators contain at least one scraper (e.g., two or three scrapers).

The design of the applicators and also of the scrapers functioning as collimators is not simply to be considered as a beam-geometric problem, since the scattering has a clear influence on the beam shape. A significant amount of thought was therefore put into the geometric design of applicators and/or consecutive scrapers. One problem, however, is the choice of material for the scrapers, since the beam-physical properties with respect to the field distribution and the lateral leakage radiation of the applicators is also to be considered. Electron applicators that include two or three scrapers made of a homogenous material are therefore used. Certain materials (e.g., metals) are taken into consideration, however, which result in a high weight of the scrapers and thus of the applicators. Brief descriptions of applicators and scrapers in the medical radiation treatment field are found, for example, in an article by L. J. van Battum et al., Phys. Med. Biol. 48 (2003) 2493-2507 or in ICRU Report 35, 2. reprint, 1992, Chapter 3.

SUMMARY AND DESCRIPTION

The present embodiments may obviate one or more of the drawbacks or limitations in the related art. For example, a scraper for an electron applicator that has a minimal weight and has improved beam-physical properties is provided.

A scraper for an applicator is used in electron radiation therapy. The scraper is structured in a three layer arrangement. The three layer arrangement includes a first layer, a second layer (e.g., a middle layer), and a third layer. The first layer faces an incident direction of the electrons and is a first material having a first atomic number. The first atomic number is smaller than a second atomic number of a second material of the second layer. The second atomic number is smaller than a third atomic number of a third material of the third layer, which faces away from the incident direction of the electrons. The first atomic number is in a region below 14 and/or the second atomic number is in a region of 14-50 and/or the third atomic number is in a region above 50.

The necessary beam-physical properties of the scraper may also be achieved by an appropriate choice of material and a structure of the scraper in a three layer construction (e.g., a combination of several materials in a multilayer arrangement). The term "atomic number" is to be understood as the mean atomic number for several materials containing elements. Consequently, materials such as, for example, plastic may also be assigned an atomic number (e.g., a mean atomic number). A layer (e.g., the first layer) of a material of a low atomic number (e.g., lower than 14), a layer (e.g., the second layer) of a medium-heavy material of a second atomic number (e.g., 14 to 50), and a layer (e.g., the third layer) of a material of a high atomic number (e.g., above 50), may follow one another in the incident direction. It is then simultaneously possible to reduce the weight of the scraper and thus of the applicator and to achieve improved beam-physical properties. With the present embodiment, the homogenous field distribution also remains, and the lateral leakage radiation is reduced by slight induced secondary radiation.

The present embodiments are based, in part, on the different interactive behavior as a function of the atomic numbers. The stopping power of low-energy charged particles (e.g., electrons) may be calculated by way of the Bethe-Bloch formula. The stopping power for light elements is greater for elements of a higher atomic number, since the ratio of the atomic number and mass number decreases with increasing atomic number. A further effect is that with high atomic numbers, binding energies for the inner shell electrons reduce and thus the probability of interactions also reduce.

The materials with a higher atomic number exhibit the best stopping power in a region of higher kinetic energy of the electrons. This is why materials with a higher atomic number are used in the scrapers. The three materials cited in the layers advantageously complement each other in terms of functionality. The first material of a low atomic number reduces the scattered radiation portion of low energy electrons so that the patient dose is likewise reduced outside of the radiation field. Consequently, an improvement in terms of the dose to the patient is achieved by low energy electrons by the layer having a material of a low atomic number. The second medium-heavy material of the second atomic number is the material that is actually used for beam shaping. A portion of electrons is scattered back into the beam, and the electron beam is collimated within the radiation field. This material ultimately represents the optimum between the conflicting objectives: low bremsstrahlung generation; and low scattered radiation portion of low energy protons. The layer facing the surface to be radiated (e.g., the third layer) including the third material that has the third atomic number (e.g., a high atomic number), is used to reduce bremsstrahlung photons, so that the patient dose is further reduced outside of the radiation field.

Not only a reduction in the scraper weight exists but improvements with respect to the beam guidance also appear, since lateral leakage radiation from the first material may be reduced by minimally induced secondary radiation (e.g., through the first layer made of the first material).

In another embodiment, the first material may be a plastic (e.g., polyethylene) and/or aluminum, and/or the second material may be copper, iron, steel, or a combination thereof, and/or the third material may be tungsten and/or lead. These materials may be well suited to the design of the scraper with the improved properties in accordance with the compound.

With respect to the layer thicknesses, the layer of the first material may include a thickness of 1-20 mm and/or the layer of the second material may include a thickness of 3-20 mm and/or the layer of the third material may include a thickness of 1-7 mm. A thinner layer of the third material may be used so that the third layer may be thinner than the layers including the first material and the second material. For example, the middle layer may include the greatest thickness, since the middle layer undertakes the main beam-shaping task, as already described.

In addition to the scraper, the present embodiments also relate to an electronic applicator, including at least one embodiment of a scraper (e.g., two or three scrapers of the present embodiments). All embodiments with respect to the scraper may be similarly applied to the electron applicator of the present embodiments. The electron applicator is consequently reduced in terms of weight and includes improved beam-physical properties.

DETAILED DESCRIPTION OF THE DRAWINGS

Figure 1:
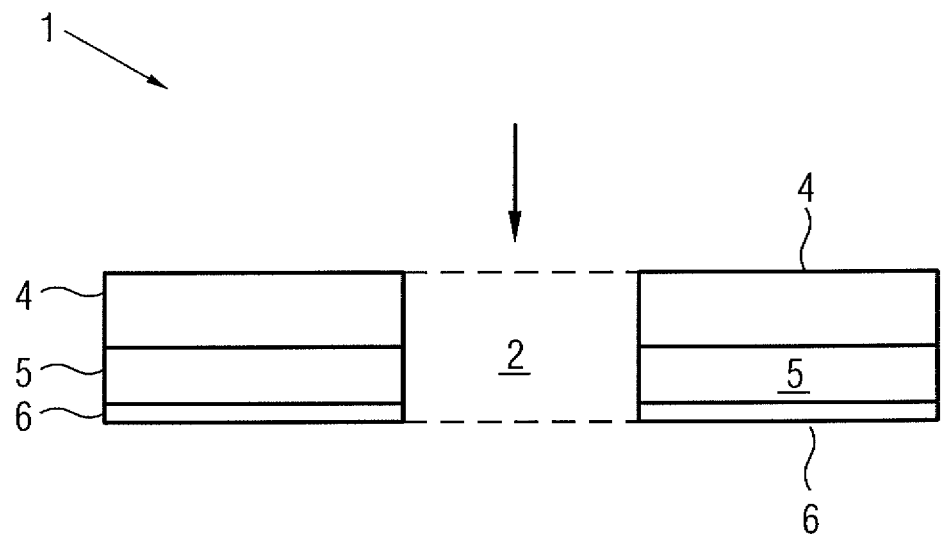
FIG. 1 shows a schematic diagram of one embodiment of a scraper.

FIG. 1 shows a schematic diagram of one embodiment of a scraper 1. The scraper is used as part of an electron applicator adjacent to a surface to be radiated (e.g., skin of a patient) in order to keep the radiation dose outside of the surface to be irradiated as minimal as possible. The scraper 1 includes a central through-hole 2, through which an electron beam, the direction 3 of which is indicated, may pass.

The scraper 1 is embodied as a multi-layer arrangement. A layer 4 (e.g., a first layer) facing an entry direction 3 is made of, for example, polyethylene (e.g., a first material). The first layer 4 consequently includes a much lower mean atomic number (e.g., below 14). In one embodiment, the first layer 4 layer is, for example, 10 mm thick.

In one embodiment, a middle layer 5 (e.g., a second layer) that is made of a medium-heavy material (e.g., a second material such as iron or steel) of a second atomic number is, for example, 7 mm thick. A layer 6 (e.g., a third layer) made of a material (e.g., a third material) of a high atomic number (e.g., greater than 50) such as, for example, lead connects hereto facing away from the entry direction 3 of the electron beam. In one embodiment, the third layer 6 is, for example, thinner and approximately 3 mm thick.

The precise geometric embodiment and the exact layer thicknesses used may ultimately be determined for each application case in an optimization method.

Figure 2:
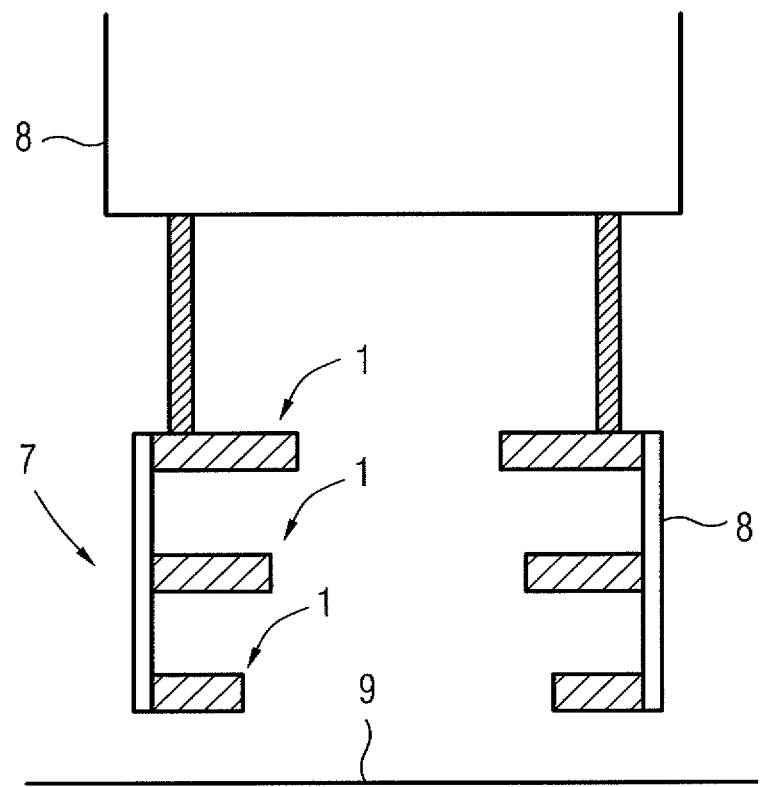
FIG. 2 shows one embodiment of an electron applicator.

FIG. 2 shows a schematic drawing of an electron applicator 7 that connects to an exit region 8 of an electron beam preparation facility.

The electron applicator 7 is essentially arranged adjacent to a surface 9 to be irradiated (e.g., a patient surface). The electron applicator 7 includes three consecutive, slightly differently embodied scrapers 1 of the present embodiments on a support structure 8. The support structure may also define a laterally closed housing. The three layer structure of the scraper 1 is not shown here in detail for reasons of clarity.

Using the three layers 4, 5, 6, applicators 7 including a minimal weight may be produced. The beam behavior is also improved, since the first layer 4 with the first material of a lower atomic number reduces a scattering radiation portion of low energy electrons, the second layer 5 with the medium-heavy material adopts the actual beam shaping task, and the third layer 6 with the third material of a high atomic number significantly reduces the bremsstrahlung photons (e.g., deceleration radiation) on account of a quadratic dependence on the atomic number.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A scraper for an applicator to be used in electron radiation therapy, the scraper comprising:
   a three layer arrangement comprising:
      a first layer that is an outermost layer facing an incident direction of electrons, the first layer comprising a first material and having a first atomic number;
      a second layer comprising a second material and having a second atomic number; and
      a third layer that is an outermost layer facing away from the incident direction of the electrons, the third layer comprising a third material and having a third atomic number, the second layer being disposed between the first layer and the third layer,
   wherein the first atomic number is smaller than the second atomic number, and the second atomic number is smaller than the third atomic number.

2. The scraper as claimed in claim 1, wherein the first atomic number is below 15, the second atomic number is 15 to 50, the third atomic number is above 50, or a combination thereof.

3. The scraper as claimed in claim 1, wherein the first material is plastic, aluminum, or a combination thereof, the second material is copper, iron, or a combination thereof, the third material is tungsten, lead, or a combination thereof, or a combination thereof.

4. The scraper as claimed in claim 1, wherein the first layer comprises a thickness of 1 to 20 mm, the second layer comprises a thickness of 3 to 20 mm, the third layer comprises a thickness of 1 to 7 mm, or a combination thereof.

5. The scraper as claimed in claim 2, wherein the first material is plastic, aluminum, or a combination thereof, the second material is copper, iron, or a combination thereof, the third material is tungsten, lead, or a combination thereof, or a combination thereof.

6. The scraper as claimed in claim 2, wherein the first layer comprises a thickness of 1 to 20 mm, the second layer comprises a thickness of 3 to 20 mm, the third layer comprises a thickness of 1 to 7 mm, or a combination thereof.

7. The scraper as claimed in claim 3, wherein the first layer comprises a thickness of 1 to 20 mm, the second layer comprises a thickness of 3 to 20 mm, the third layer comprises a thickness of 1 to 7 mm, or a combination thereof.

8. An electron applicator comprising:
   at least one scraper comprising:
      a three layer arrangement comprising:
         a first layer that is an outermost layer and facing an incident direction of electrons, the first layer comprising a first material and having a first atomic number;
         a second layer comprising a second material and having a second atomic number; and
         a third layer that is an outermost layer facing away from the incident direction of the electrons, the third layer comprising a third material and having a third atomic number, the second layer being disposed between the first layer and the third layer, wherein the first atomic number is smaller than the second atomic number, and the second atomic number is smaller than the third atomic number.

9. The electron applicator as claimed in claim 8, wherein the at least one scraper comprises two or three scrapers.

10. The scraper as claimed in claim 1, wherein a thickness of the second layer is greater than a thickness of the first layer and a thickness of the third layer.

11. The scraper as claimed in claim 10, wherein the thickness of the third layer is less than the thickness of the first layer.

12. The scraper as claimed in claim 1, wherein the first material is configured to reduce a scattering radiation portion of a first group of the electrons, the second material is configured to scatter a second group of the electrons into an electron beam, and the third material is configured to reduce bremsstrahlung photons, the electrons forming the electron beam.

\* \* \* \* \*